United States Patent [19]

McRae

[11] Patent Number: Plant 5,990

[45] Date of Patent: May 19, 1987

[54] ASIATIC LILY NAMED JOANNA

[75] Inventor: Edward A. McRae, Boring, Oreg.

[73] Assignee: Melridge Inc., Gresham, Oreg.

[21] Appl. No.: 710,457

[22] Filed: Mar. 11, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler; John B. Lungmus

[57] ABSTRACT

A new variety of Asiatic hybrid lily having flowers of excellent form and large size, particularly characterized by an unusual combination of yellow and gold color tones and having a very sparse maculation of rather light spots, a color pattern that is new in the upright Asiatic division of lilies. The flowers also have long persistence, both on the plant and as cut flowers. The plant is highly resistant to disease, shows high tolerance to virus, and is an excellent garden plant. The bulbs may be precooled and forced for cut-flower production, blooming earlier than those of siblings similar in appearance, thereby extending the season of cut-flower production.

1 Drawing Figure

BACKGROUND OF THE INVENTION

This new variety of lily plant originated as a seedling selected from a group of seedlings resulting from my cross of the species *Lilium wilsonii* var. *flavum* and the cultivar "Connecticut King" in the course of breeding efforts carried on by me at Sandy, Oreg., since 1971 with the object of producing superior, upright-flowering Asiatic lilies with shades of yellow and gold coloration and suited to cut-flower production and to forcing so as to extend the range of flowering times for cut-flowers.

This particular seedling was selected for propagation because of the large size of its flowers, which had very broad petals of thick texture and an unusual color pattern which appears on both petals and sepals, each yellow tepal being flushed with gold at its base and having very light spotting on each side of the outer end of the nectary channel, appearing particularly in the petals. Also, this seedling appeared to possess all of the desired characteristics of form, color, and habit. For these reasons, this seedling has been asexually reproduced by me and under my direction at Sandy, Oreg., and successive generations produced by bulb-scale propagation and natural propagation from bulblets have demonstrated that this new plant possesses the desirable characteristics of hybrid vigor, great hardiness, and a high degree of disease resistance, the clone being a vigorous and good grower and propagator, as observed at Sandy, Oreg. These successive generations of production have also demonstrated that the novel and distinctive characteristics of this new variety hold true under asexual propagation from generation to generation and appear to be firmly fixed.

DESCRIPTION OF THE DRAWING

The new variety of lily plant herein disclosed is illustrated in the accompanying photographic drawing, which shows a face view of a fully opened bloom, together with several buds in various stages of development. The bloom illustrating the flower form and tepal arrangement has been hand-painted to show, in particular, the novel and distinctive yellow and gold pattern and the relatively light maculation of its unusually broad petals.

DESCRIPTION OF THE NEW PLANT

The following is a detailed description of my new variety of hybrid Asiatic lily with color designations according to The R.H.S. Colour Chart published by The Royal Horticultural Society of London, England, and with nomenclature according to The International Lily Register, Second Edition, of The Royal Horticultural Society.

THE PLANT

Origin: Seedling.

Parentage:

- *Seed parent.*—*Lilium wilsonii* var. *flavum* (unpatented).
- *Pollen parent.*—"Connecticut King" (unpatented).

Classification:

- *Horticultural.*—Hybrid lily cultivar, Division I-A of the Horticultural Classification of Lilies by The Royal Horticultural Society.
- *Commercial.*—Asiatic hybrid lily.

Form: Single stem, erect, and stately.

Height: About 120 to 170 cm. from bulbs about 15 to 20 cm. in circumference.

Growth: Vigorous and upright.

Foliage:

- *Quantity.*—Abundant.
- *Leaf size.*—About 8 to 12 cm. long and about 1.5 to 2 cm. at its sessile base.
- *Leaf shape.*—Lanceolate.
- *Texture.*—Leathery.
- *Aspect.*—Glossy.
- *Color.*—Upper and lower sides, medium green.

Bulbs:

- *Size.*—Ranging to about 25 cm. in circumference in commercial use.
- *Color.*—White.

THE BUD

Form: Oblong with obtuse base and tip ends.

Size: About 7 to 9 cm. long just prior to opening.

Opening rate: Slow, about one hour at maturity in response to light.

Color: Medium to deep yellow when sepals first divide and when tepals begin to unfurl.

*Tepals when unfurling.*—Medium to deep yellow on upper and lower surfaces with the upper surface flushed with gold adjacent the outer end of the nectary.

Peduncle:

*Length.*—About 7.5 to 10 cm. depending upon light levels.

*Color.*—Medium green.

THE FLOWER

Blooming habit: Annually in early mid-season for Asiatic lilies. October-dug bulbs, properly precooled, planted in February under glass in western Oregon, and with no supplementary lighting, flower in an average of about 80 days.

Size: Large; 15 to 18 cm. in diameter.

Borne: As a compact raceme of about 5 to 7 buds on a single stem. The inflorescence may carry secondary buds.

Shape: Generally flat to slightly dished with tepal tips lightly recurved.

Tepalage:

*Number.*—Six.

*Arrangement.*—Petals offset about sixty degrees from the sepals with the margins of the base portions narrowly overlapping the margins of the sepals.

Color: The base color of the tepals is Yellow, R.H.S. 12 A-B, each tepal having a flush of Gold, R.H.S. 21A, about 2 cm. wide and 2 cm. long extending along its midrib from above the nectary, each petal also having a few small spots of deep magenta color adjacent each side of the end of the nectary.

Color change: As the flower ages, its color intensifies slightly and may become more golden-toned under low light levels.

Tepal longevity: Tepals stay on the stem about three weeks.

Pedicels:

*Length.*—About 4 to 6 cm.; secondary buds may have shorter pedicels.

*Form.*—Sturdy and upright.

*Color.*—Light green.

Fragrance: None.

Disease resistance: The flower and plant are resistant to disease, and in particular, they are resistant to Fusarium and Botrytis.

Lasting quality: The flower is long lasting, both on the plant and as a cut flower.

THE REPRODUCTIVE ORGANS

Stamens:

*Number.*—Six.

*Arrangement.*—Typical of genus Lilium.

Anthers:

*Color.*—Greyed Gold, R.H.S. 167A.

Filaments:

*Length.*—About 5 cm.

*Color.*—Ivory or yellow.

Pollen:

*Color.*—Greyed Gold, R.H.S. 167A.

Pistils:

*Number.*—One.

Style:

*Length.*—About 5 cm.

Stigma: Light plum to gold in color.

Ovary: Typical of genus Lilium.

THE FRUIT

Fertility: The fruit is fertile.

Shape: Ovoid.

Color at maturity: Soft brown, sometimes overlaid with light plum.

This new variety of Asiatic hybrid lily most nearly resembles the cultivar "Connecticut King" but has much broader petals each having a few spots, is taller in its growth and is superior for year around forcing. This new variety flowers somewhat later than does "Connecticut King" but earlier than any of its siblings which have been selected for general commercial cut-flower production, thereby extending the cut-flower season for this type lily.

Distinguishing Characteristics of Siblings
From the Cross *Lilium Wilsonii* var. *flavum* x "Connecticut King"

| Cv | Days to Bloom | Buds | Maculation |
|---|---|---|---|
| Pollyanna Serial No. 710,427 | 80–85 | 5–8 | Heavy, large. |
| Joanna Serial No. 710,457 | 80 | 5–7 | Light |
| Adelina Serial No. 710,614 | 80–85 | 6–8 | Very few and small. Of deep magenta color. |
| Vanessa Serial No. 710,496 | 90–95 | 5–8 | Very light |
| Yolanda Serial No. 710,577 | 95–100 | 5–8 | Sparse and of deep magenta color. |
| Gold Medal (Half Sib) Serial No. 710,592) | 60–70 | 6–8 | Few, tiny |

| Cv | Other Notable Characteristics |
|---|---|
| Pollyanna Serial No. 710,427 | Relatively narrow, widely spaced tepals and sepals with very little marginal overlapping. Arrangement, hexagonal. |
| Joanna Serial No. 710,457 | Tepal-sepal angle 60°. Arrangement, generally imbricated. |
| Adelina Serial No. 710,614 | Tepals are large, thick textured, relatively broad, and with lightly recurved tips. Arrangement, imbricated. |
| Vanessa Serial No. 710,496 | Tepals have slightly recurved tips and inconspicuous maculation. Arrangement, uniformly imbricated. |
| Yolanda Serial No. 710,577 | Larger bulb, flower dished with tepal-sepal angle 60°, with lightly overlapping arrangement. |
| Gold Medal (Half Sib) Serial No. 710,592) | Very thick and broad tepals in 60° overlapping arrangement with sepals. Unusually long lasting flowers, bud blast resistant when forced, and attains large bulb size only in season. |

I claim:

1. A new variety of Asiatic lily plant, substantially as herein shown and described, characterized by its yellow and gold flower color pattern and its light maculation, which are unique in the Asiatic hybrid lily division of lilies suited for forcing; the plant is also characterized by its vigorous growth and propagation habit, its unique early mid-season time of flowering, and its high resistance to disease and high tolerance to virus.

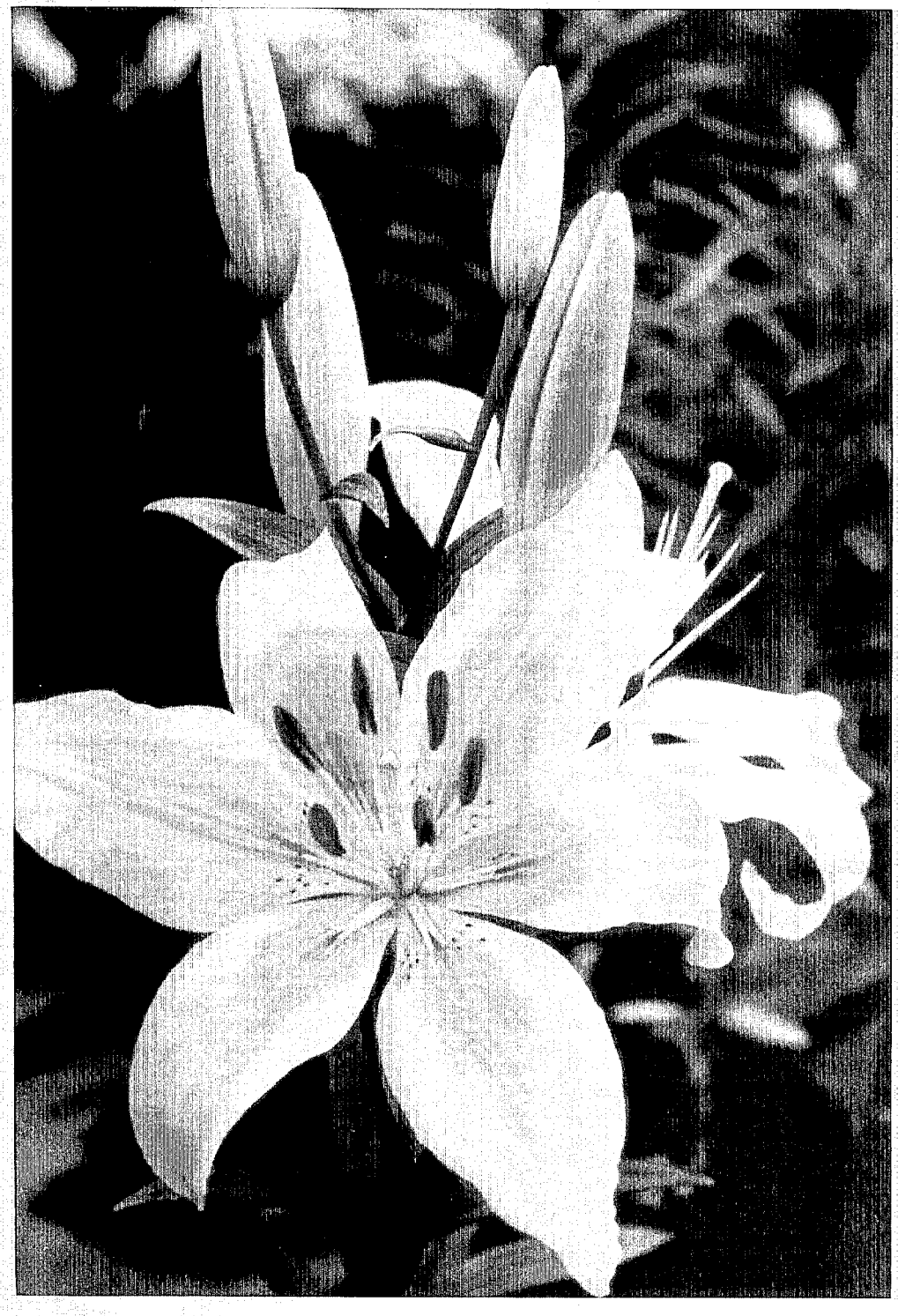

* * * * *